(12) United States Patent
Ahn et al.

(10) Patent No.: US 12,741,089 B2
(45) Date of Patent: Sep. 22, 2026

(54) DRIP INFUSION CONTAINER FOR INFUSION DEVICE

(71) Applicant: Jae Hyung Ahn, Seoul (KR)

(72) Inventors: Jae Hyung Ahn, Seoul (KR); Sungkwan An, Seoul (KR)

(73) Assignee: Jae Hyung Ahn, Seoul (KR)

( * ) Notice: Subject to any disclaimer, the term of this patent is extended or adjusted under 35 U.S.C. 154(b) by 382 days.

(21) Appl. No.: 18/686,738

(22) PCT Filed: Aug. 31, 2022

(86) PCT No.: PCT/KR2022/012992
§ 371 (c)(1),
(2) Date: Feb. 26, 2024

(87) PCT Pub. No.: WO2023/033530
PCT Pub. Date: Mar. 9, 2023

(65) Prior Publication Data
US 2025/0135108 A1 May 1, 2025

(30) Foreign Application Priority Data
Sep. 1, 2021 (KR) ........................ 10-2021-0116475
Aug. 29, 2022 (KR) ........................ 10-2022-0108557

(51) Int. Cl.
*A61M 5/158* (2006.01)

(52) U.S. Cl.
CPC ......... *A61M 5/158* (2013.01); *A61M 2207/10* (2013.01)

(58) Field of Classification Search
CPC ............................ A61M 5/158; A61M 5/1411
See application file for complete search history.

(56) References Cited

U.S. PATENT DOCUMENTS

| | | | | |
|---|---|---|---|---|
| 5,423,346 A * | 6/1995 | Daoud | A61M 5/40 | 137/433 |
| 6,337,631 B1 * | 1/2002 | Pai | A61M 5/1411 | 604/254 |
| 2006/0129111 A1 * | 6/2006 | Mottola | A61M 5/36 | 604/254 |
| 2009/0259199 A1 * | 10/2009 | Lampropoulos | A61M 5/1412 | 604/246 |

FOREIGN PATENT DOCUMENTS

| | | |
|---|---|---|
| JP | 5-7244 U | 2/1993 |
| KR | 20-0188631 Y1 | 7/2000 |
| KR | 20-0257313 Y1 | 12/2001 |

(Continued)

OTHER PUBLICATIONS

Office Action from corresponding Korean Patent Application No. 10-2022-0108557 dated Oct. 9, 2024. (Google Translation).

(Continued)

*Primary Examiner* — Dung T Ulsh
(74) *Attorney, Agent, or Firm* — Christensen, Fonder, Dardi, Busse; Diane E. Bennett; Peter S. Dardi

(57) ABSTRACT

The present invention relates to a drip infusion container for an infusion device and, more particularly, to a drip infusion container capable of preventing accidents such as air being injected to a patient when infusion is finished or a problem occurs in infusion discharge from an infusion bag.

11 Claims, 9 Drawing Sheets

(56) References Cited

FOREIGN PATENT DOCUMENTS

| | | | |
|---|---|---|---|
| KR | 10-2002-0066163 | A | 8/2002 |
| KR | 10-0432865 | B1 | 5/2004 |
| KR | 10-1027081 | B1 | 4/2011 |
| KR | 10-1346521 | B1 | 12/2013 |
| KR | 10-1740918 | B1 | 5/2017 |
| KR | 10-2018-0127883 | A | 11/2018 |

OTHER PUBLICATIONS

International Search Report from corresponding Patent Application No. PCT/KR2022/012992 dated Dec. 19, 2022.

* cited by examiner

DRIP INFUSION CONTAINER FOR INFUSION DEVICE

CROSS REFERENCE TO RELATED APPLICATIONS

The present application is a National Stage filing of PCT Application No. PCT/KR2022/012992 filed Aug. 31, 2022, entitled "Drip Infusion Container for Infusion Device", which claims the benefit of priority based on Korean Patent Application No. 10-2021-0116475 filed on Sep. 1, 2021 and Korean Patent Application No. 10-2022-0108557 filed on Aug. 29, 2022, the entire disclosures of which are incorporated as a part of this specification.

TECHNICAL FIELD

The present disclosure relates to a drip infusion container for an infusion device, and more particularly, to a drip infusion container for an infusion device capable of preventing accidents such as air being injected to a patient when infusion is finished or there is a problem with infusion discharge from an infusion bag.

BACKGROUND ART

An infusion device may be used for patients who cannot take drugs or food by mouth due to problems with the digestive system or lack of consciousness. Specifically, an artificial solution may be injected intravenously or subcutaneously rather than through the mouth, and the artificial solution may be injected into the patient over several minutes to several hours.

At this time, when an infusion is emptied or there is a problem with a flow path of the infusion, air, rather than the infusion, may be injected into the patient. When air enters a vein, it may block the blood vessel, which may cause dysfunction or, in severe cases, lead to death.

For example, medical professionals are also very concerned about medical accidents that occur when they do not recognize in time that the infusion in an infusion bottle (bag) is empty, and in fact, infusion accidents related to this often occur. In particular, in the case of night and at the site of civilian and military emergency measures, it is often not possible to check individually whether the infusion in the infusion bottle (bag) and an infusion line is depleted.

Due to fear of this, patients and their guardians always nervously check a state of the infusion in the infusion bottle (bag) and an infusion tube, and often ask for help from medical staff such as nurses by timing the infusion bottle (bag) to be emptied.

Therefore, there is a need for a technology for preventing air from entering the patient's blood vessel when injection of the infusion is finished or there is a problem with an infusion bag and an infusion injection flow path.

DISCLOSURE OF THE INVENTION

Technical Goals

The present disclosure relates to a drip infusion container for an infusion device, and more particularly, to a drip infusion container for an infusion device capable of preventing accidents such as air being injected to a patient's vessel when infusion is finished or there is a problem with infusion discharge from an infusion bag.

Technical objects to be achieved by the present disclosure are not limited to the technical objects mentioned above, and other technical objects not mentioned will be clearly understood by those skilled in the art from the description below.

Technical Solutions

A drip infusion container for an infusion device of the present disclosure may include:

- an introduction needle which extends in a vertical direction and whose upper end is inserted into an infusion-fluid container in which infusion is stored;
- a transparent container which extends in the vertical direction and receives the infusion through the introduction needle; and
- a control ball which is located inside the transparent container and provided with a specific gravity lower than that of the infusion.

Advantageous Effects

A drip infusion container for an infusion device of the present disclosure may be capable of preventing accidents such as air being injected to a patient when infusion is finished or there is a problem with infusion discharge from an infusion bag.

BEST MODE FOR CARRYING OUT THE INVENTION

Figure 1:
FIG. 1 is a perspective view illustrating a drip infusion container for an infusion device of the present disclosure.
Figure 1:
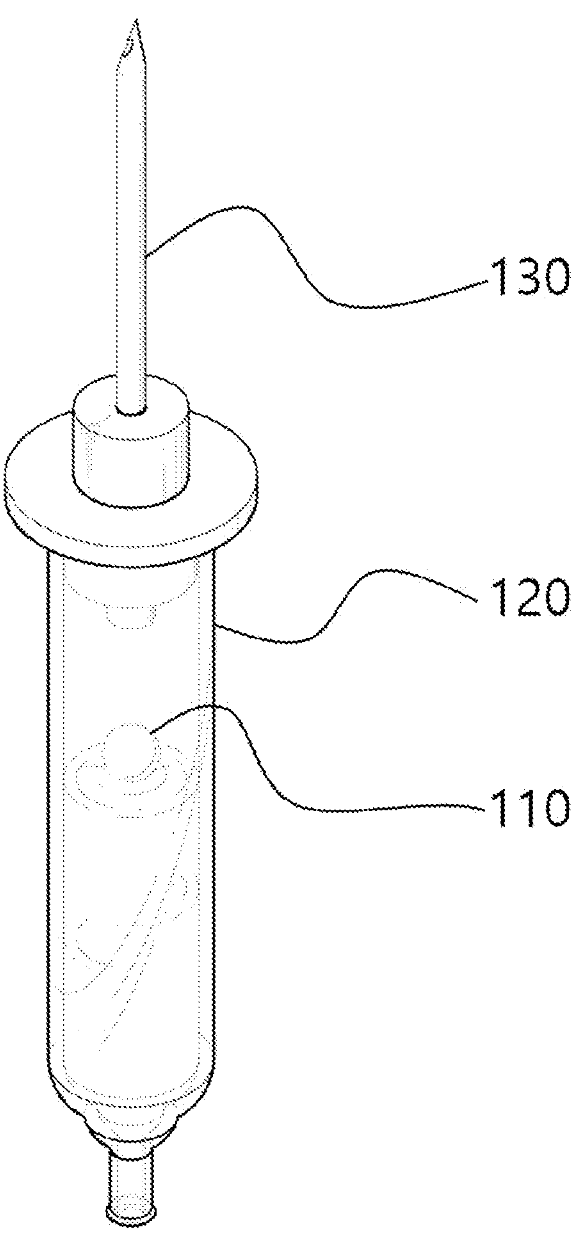

A drip infusion container for an infusion device of the present disclosure may include:

- an introduction needle which extends in a vertical direction and whose upper end is inserted into an infusion-fluid container in which infusion is stored;
- a transparent container which extends in the vertical direction and receives the infusion through the introduction needle; and
- a control ball which is located inside the transparent container and provided with a specific gravity lower than that of the infusion.

In the drip infusion container for the infusion device of the present disclosure, the transparent container may include a transparent body which is provided with an infusion drop space extending in the vertical direction into which the infusion falls and has an open upper end, a stopper which is coupled to the upper end of the transparent body and to which a lower end of the introduction needle is coupled, and an outlet which is provided at a lower end of the transparent body and from which the infusion inside the transparent body is discharged.

In the drip infusion container for the infusion device of the present disclosure, a fitting groove having the same shape as a bottom surface of the control ball may be formed on an inner bottom surface of the infusion drop space of the transparent body, and an upper entrance of the outlet may be located at a center of the fitting groove.

In the drip infusion container for the infusion device of the present disclosure, the control ball may move in the vertical direction with a change in the height of a liquid level formed by the infusion in the infusion drop space, and when all of the infusion is discharged from the infusion drop space, the bottom surface of the control ball may come into close contact with the fitting groove to block the upper entrance of the outlet.

In the drip infusion container for the infusion device of the present disclosure, the control ball may include a lower member whose bottom surface is in close contact with the fitting groove, and an upper member coupled to an upper end of the lower member.

In the drip infusion container for the infusion device of the present disclosure, the upper member may be formed in a hemispherical shape with a flat bottom surface, and the lower member may be formed in a hemispherical shape with a flat upper surface.

In the drip infusion container for the infusion device of the present disclosure, the upper member may be formed in a hemispherical shape with a flat bottom surface, and the lower member may be formed in a cone shape with a flat upper surface and a vertex pointing downward.

In the drip infusion container for the infusion device of the present disclosure, the lower member may be made of a polymer produced by linking silicon to which organic groups are bonded by a siloxane bond.

In the drip infusion container for the infusion device of the present disclosure, the upper member may be formed of a material with higher hardness than the lower member, the lower member may have a coupling protrusion formed on its upper surface to be inserted into the upper member, and the upper member may have a receiving groove formed on its bottom surface into which the coupling protrusion is inserted.

In the drip infusion container for the infusion device of the present disclosure, a depth of the receiving groove may be formed to be longer than a height of the coupling protrusion, so that a hollow may be formed inside the upper member when the upper member and the lower member are coupled.

In the drip infusion container for the infusion device of the present disclosure, the coupling protrusion may be provided in a cylindrical shape, a coupling groove may be formed along a circumferential direction on a lower side of an outer peripheral surface of the coupling protrusion, and an insertion protrusion which is inserted into the coupling groove may be formed on a lower side of an inner peripheral surface of the receiving groove.

A control ball manufacturing method for manufacturing the control ball provided in the drip infusion container for the infusion device of the present disclosure may include:

a needle insertion step of inserting a suction needle from a lower side of the lower member to penetrate the lower member in the vertical direction;

a coupling step of coupling the upper member and the lower member so that the bottom surface of the upper member faces the upper surface of the lower member;

a discharge step of discharging air formed in the hollow through the suction needle; and a final step of removing the suction needle from the lower member.

In the control ball manufacturing method of the present disclosure, a hemispherical concave portion may be formed at an upper end of the coupling protrusion, and in the needle insertion step, an upper end of the suction needle may protrude from a center of the concave portion.

Modes for Carrying Out the Invention

Hereinafter, embodiments according to the present disclosure will be described in detail with reference to the accompanying drawings. In this process, the size or shape of the components shown in the drawings may be exaggerated for clarity and convenience of explanation. In addition, terms specifically defined in consideration of the configuration and operation of the present disclosure may vary according to the intentions or customs of users and operators. Definitions of these terms should be made based on the content throughout this specification.

In the description of the present disclosure, it should be noted that an orientation or positional relationship indicated by the terms such as “center”, “upper”, “lower”, “left”, “right”, “vertical”, “horizontal”, “inner side”, “outer side”, “one side”, and “other side” is based on an orientation or positional relationship shown in a drawing or an orientation or positional relationship that is placed when using the product of the present disclosure on a daily basis, and is merely for explanation and brief description of the present disclosure, and it does not suggest or imply that the displayed device or element must necessarily be configured or operated in a specified orientation and should not be construed as limiting the present disclosure.

Figure 2:
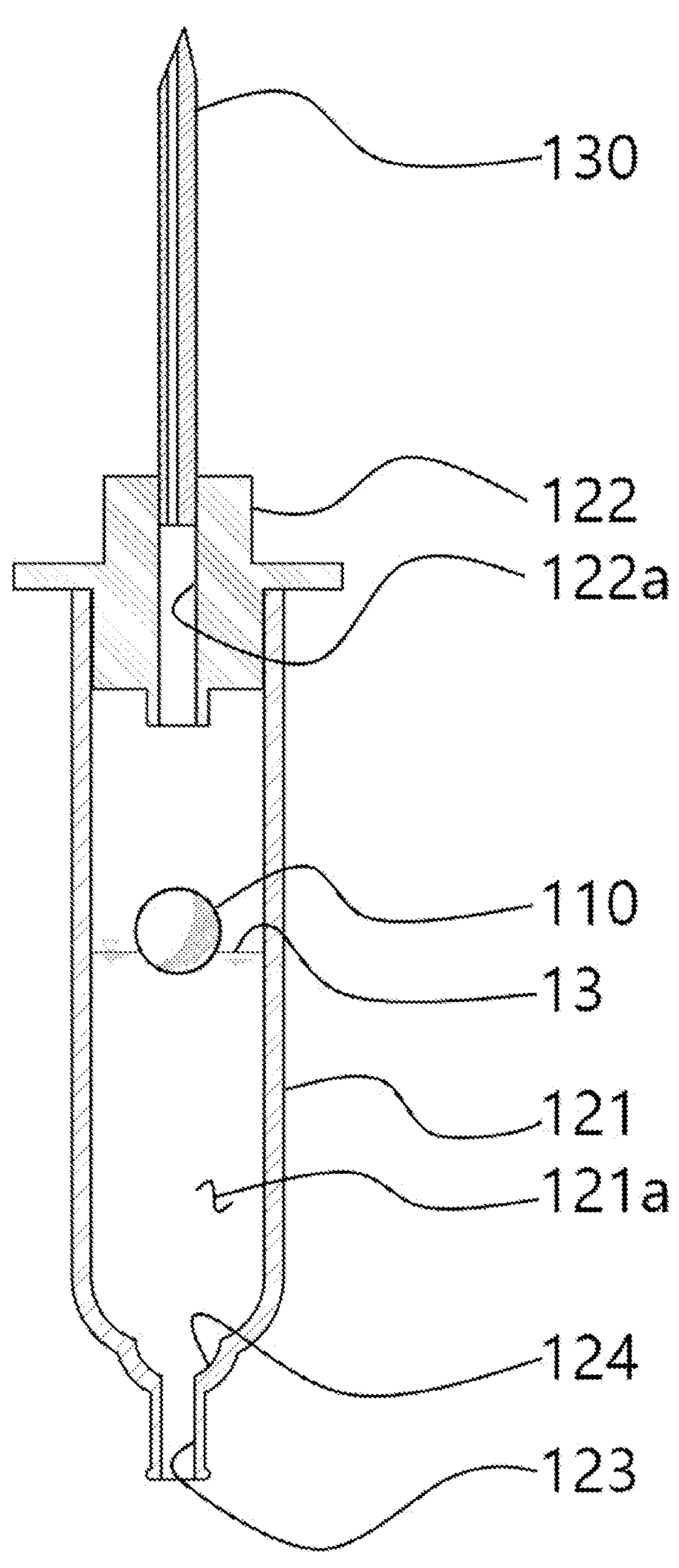
FIG. 2 is a cross-sectional view illustrating a drip infusion container for an infusion device of the present disclosure.
Figure 3:
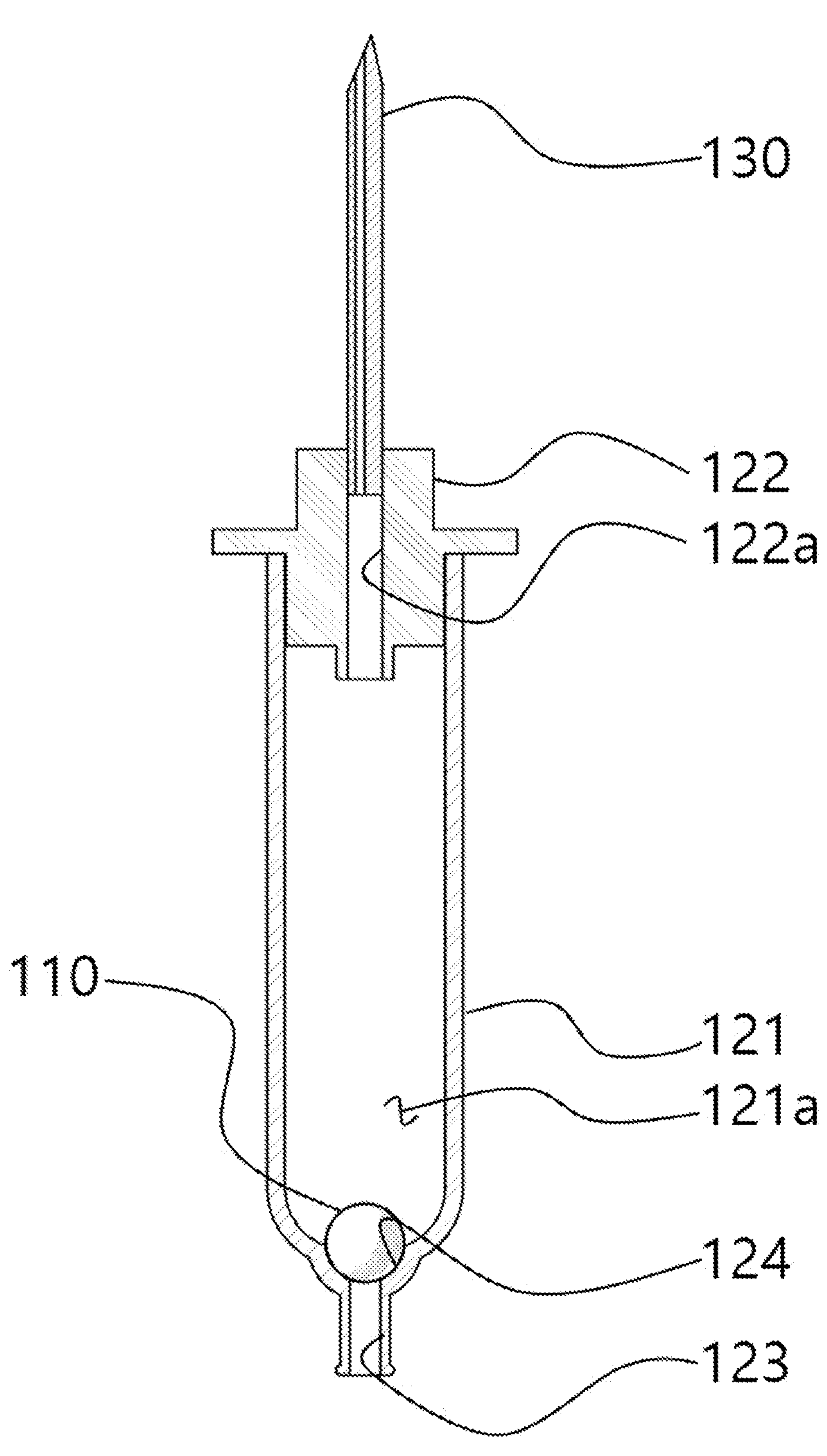
FIG. 3 is a cross-sectional view illustrating a state in which all infusion has been discharged from the drip infusion container for the infusion device of FIG. 2.
Figure 4:
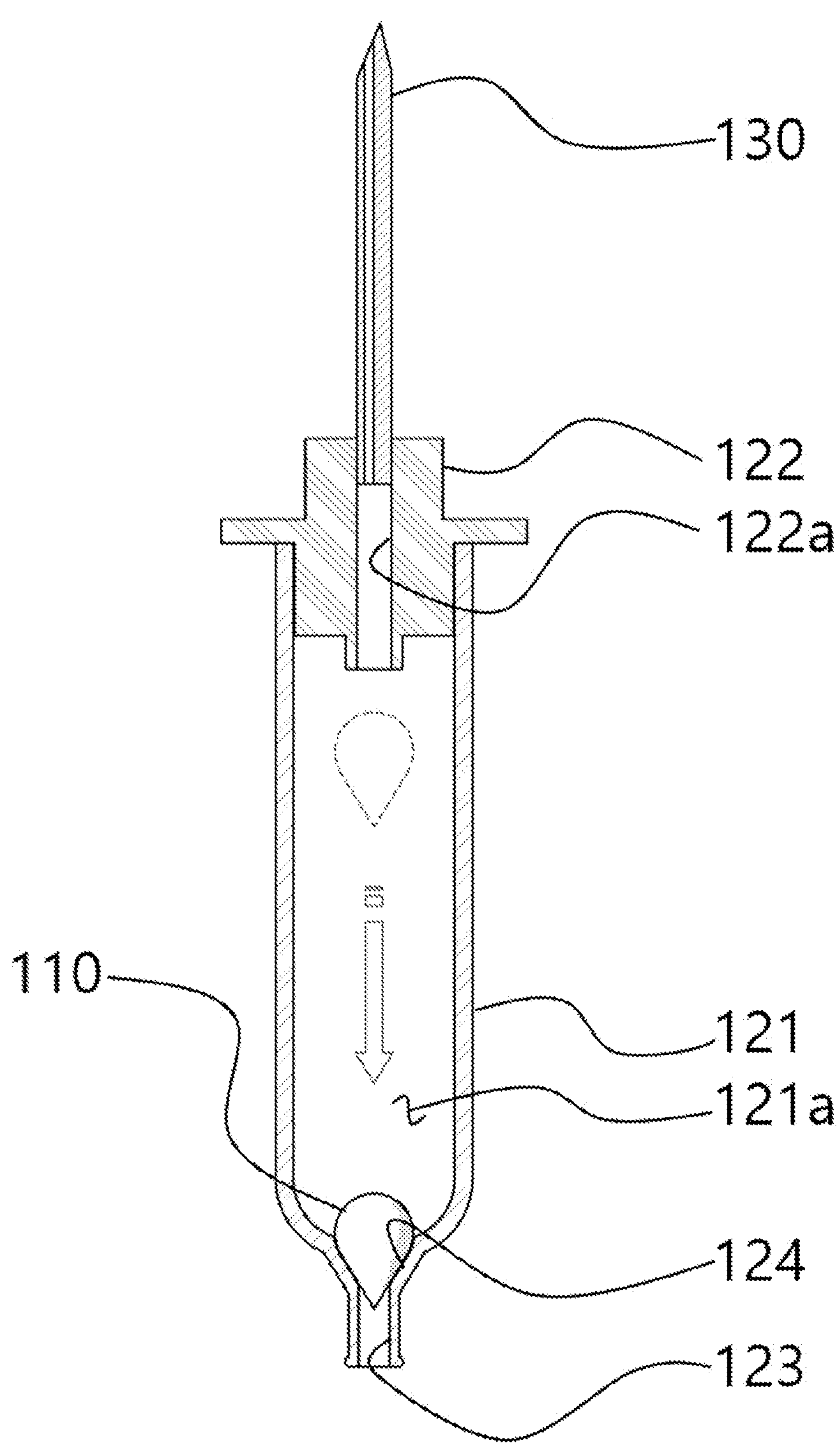
FIG. 4 is a cross-sectional view illustrating another embodiment of a drip infusion container for an infusion device of the present disclosure.
Figure 5A:
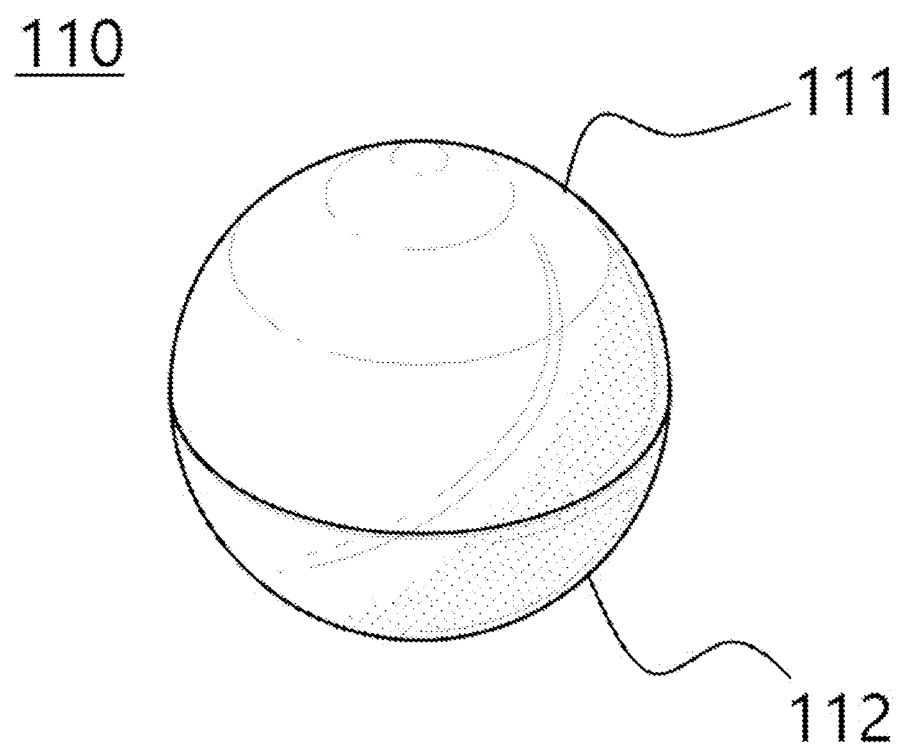
FIGS. 5A and 5B are perspective views illustrating a control ball.
Figure 5B:
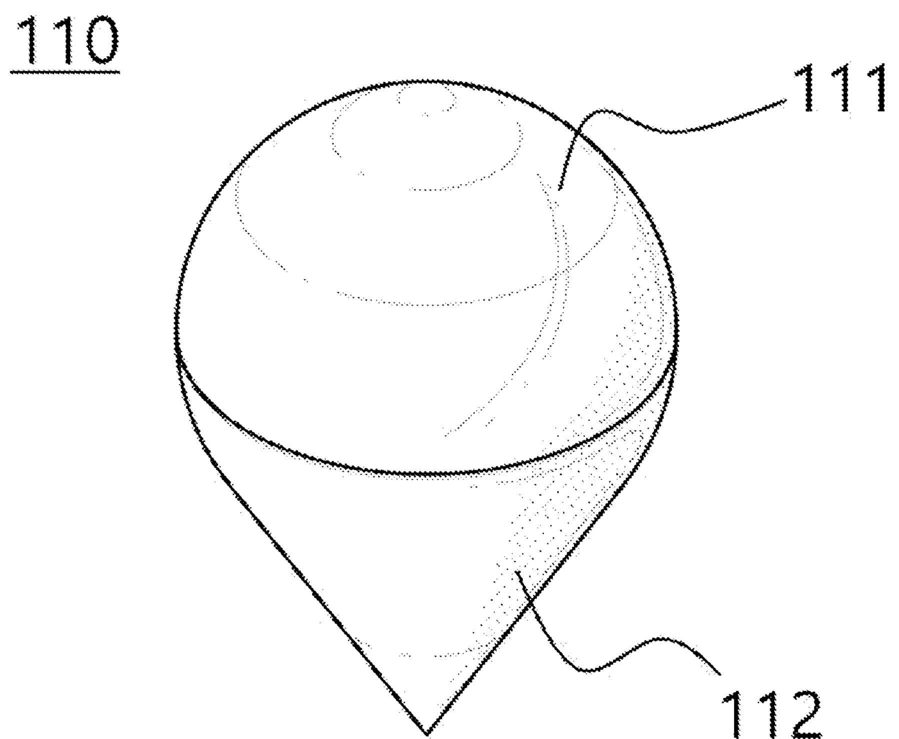
Figure 6:
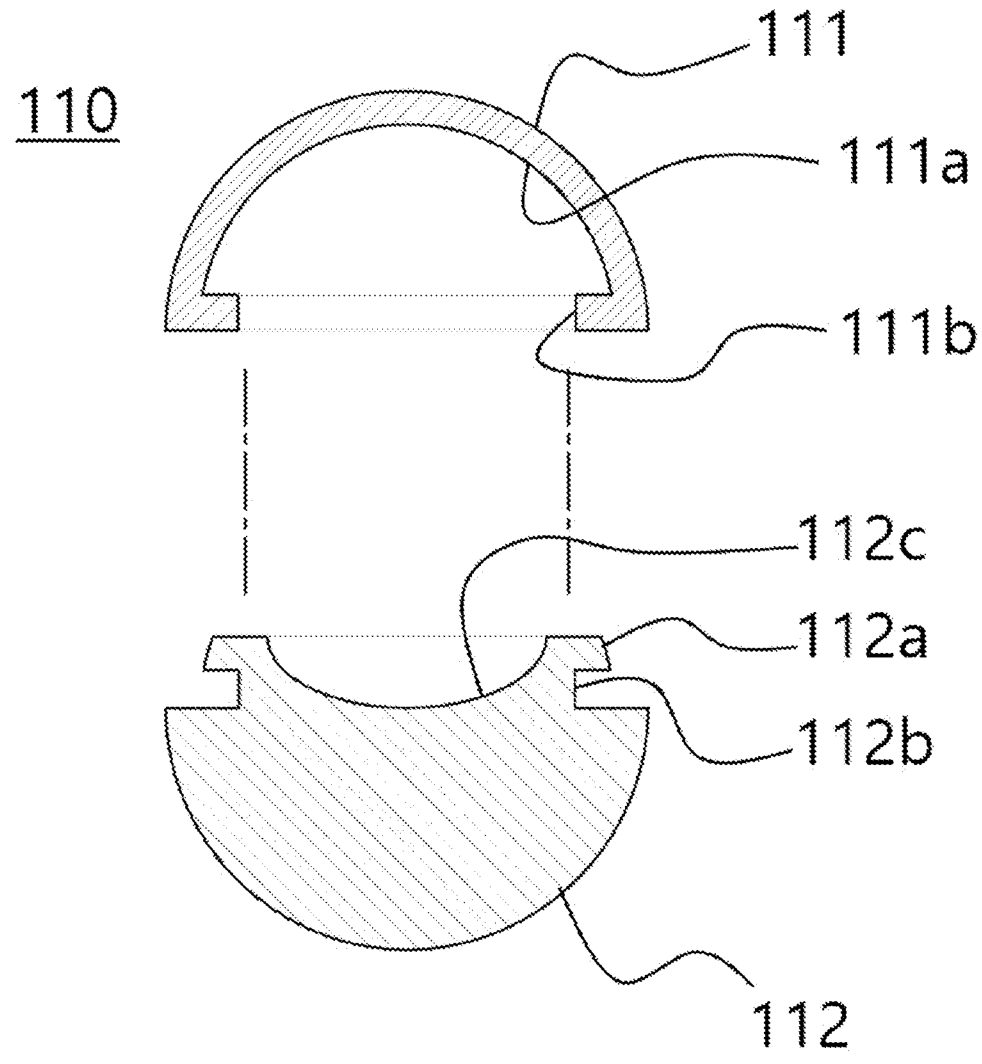
FIG. 6 is a cross-sectional view illustrating a control ball with a top member and a bottom member separated.
Figure 7:
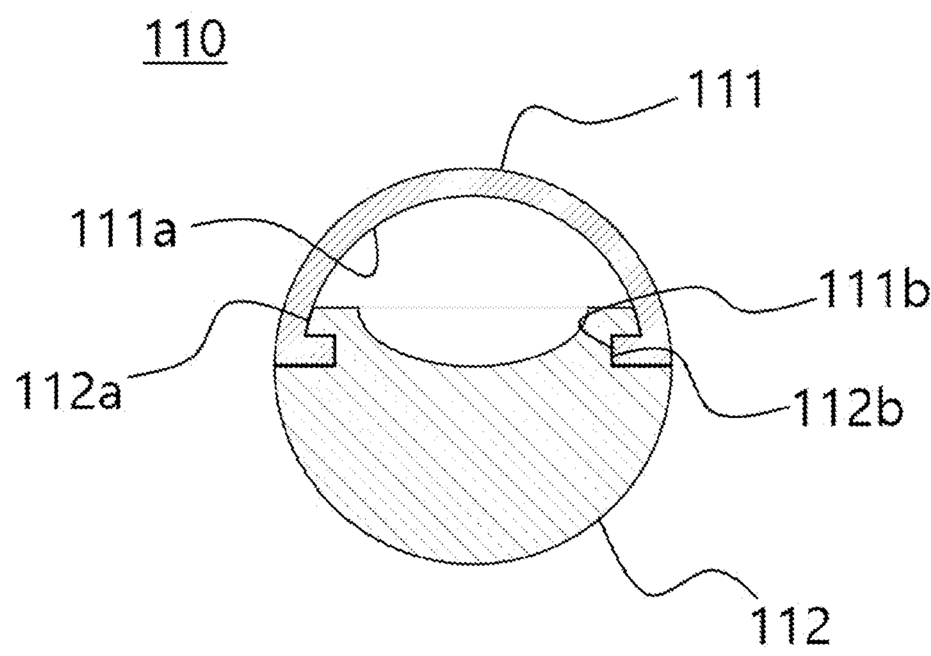
FIG. 7 is a cross-sectional view illustrating the control ball with the top member and the bottom member coupled.
Figure 8:
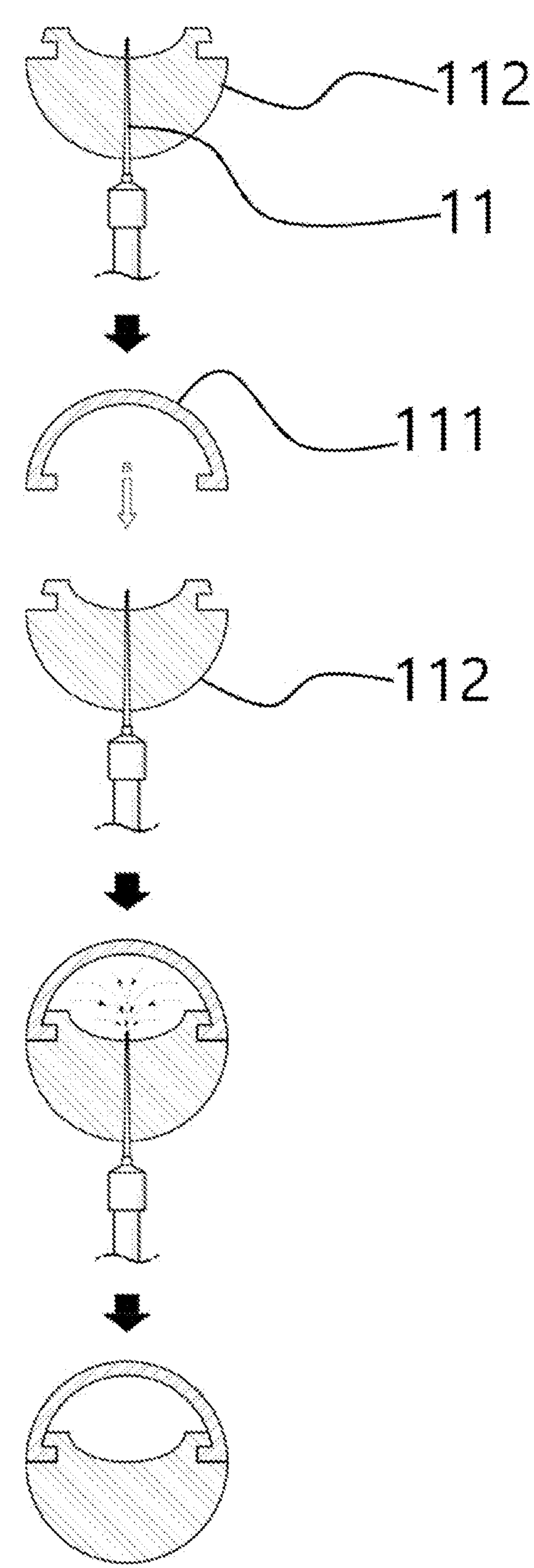
FIG. 8 is a schematic diagram illustrating a method of manufacturing a control ball provided in a drip infusion container for an infusion device of the present disclosure.

FIG. 1 is a perspective view illustrating a drip infusion container 100 for an infusion device of the present disclosure. FIG. 2 is a cross-sectional view illustrating the drip infusion container 100 for the infusion device of the present disclosure. FIG. 3 is a cross-sectional view illustrating a state in which all infusion has been discharged from the drip infusion container 100 for the infusion device of FIG. 2. FIG. 4 is a cross-sectional view illustrating another embodiment of the drip infusion container 100 for the infusion device of the present disclosure. FIGS. 5A and 5B are perspective views illustrating a control ball 110. FIG. 6 is a cross-sectional view illustrating the control ball 110 with a top member 111 and a bottom member 112 separated. FIG. 7 is a cross-sectional view illustrating the control ball 110 with the top member 111 and the bottom member 112 coupled. FIG. 8 is a schematic diagram illustrating a method of manufacturing the control ball 110 provided in the drip infusion container 100 for the infusion device of the present disclosure.

Hereinafter, the drip infusion container 100 for the infusion device of the present disclosure will be described in detail with reference to FIGS. 1 to 8.

The drip infusion container 100 for the infusion device of the present disclosure may prevent air from being injected into a patient when all infusion is used up in an infusion-fluid container (an infusion bottle, an infusion bag, etc.) in which the infusion is stored, thereby preventing accidents such as backflow of the patient’s blood. Specifically, it is possible to prevent air from being injected into the patient by blocking a flow path when the infusion is exhausted in the drip infusion container 100 for the infusion device connected to a lower end part of the infusion-fluid container.

The drip infusion container 100 for the infusion device of the present disclosure may be provided in a flow path connecting the infusion-fluid container and the patient. Specifically, the drip infusion container 100 may be installed on the lower side of the infusion-fluid container, and the infusion may be injected into the patient through the drip infusion container by gravity.

As shown in FIGS. 1 and 2, the drip infusion container 100 for the infusion device of the present disclosure may include:

- an introduction needle 130 which extends in a vertical direction and whose upper end is inserted into an infusion-fluid container in which infusion is stored;
- a transparent container 120 which extends in the vertical direction and receives the infusion through the introduction needle 130; and
- a control ball 110 which is located inside the transparent container 120 and provided with a specific gravity lower than that of the infusion.

The introduction needle 130 may be provided in a rod shape with a sharp upper end and extending in the vertical direction. A flow path extending in the vertical direction is formed inside the introduction needle 130, and the infusion of the infusion-fluid container is injected into the upper end of the introduction needle 130 and then discharged through the flow path from a lower end of the introduction needle 130, so that the infusion of the infusion-fluid container can be injected into the drip infusion container.

As shown in FIGS. 2 and 3, the transparent container 120 may include a transparent body 121 which is provided with an infusion drop space 121*a* extending in the vertical direction into which the infusion falls and has an open upper end, a stopper 122 which is coupled to the upper end of the transparent body 121 and to which the lower end of the introduction needle 130 is coupled, and an outlet 123 which is provided at a lower end of the transparent body 121 and from which the infusion inside the transparent body 121 is discharged.

Inside the transparent body 121, a hollow may be formed as the infusion drop space 121*a*. For example, the transparent body 121 may be provided in a cylindrical shape extending in the vertical direction. More specifically, the transparent body 121 may be provided in a tapered shape whose diameter becomes smaller downwards. The transparent body 121 may be provided in a shape in which its upper end is open, and as the stopper 122 is coupled to the upper end of the transparent body 121, the infusion drop space 121*a* may be formed as a closed space.

A drip infusion hole 122*a* may be formed in the stopper 122 to penetrate the stopper 122 in the vertical direction. The lower end of the introduction needle 130 may be inserted into an upper entrance of the drip infusion hole 122*a* to be coupled with the stopper 122. A lower entrance of the drip infusion hole 122*a* may protrude downward from a bottom surface of the stopper 122 and may induce the infusion injected into the drip infusion container through the introduction needle 130 to fall in the form of drops.

The transparent body 121 may be formed of a rigid material capable of transmitting visible light. Since the transparent body portion 121 is formed of a transparent material, it is possible to visually identify the state in which the infusion is falling from outside the transparent body 121.

As shown in FIGS. 2 to 4, a fitting groove 124 having the same shape as a bottom surface of the control ball 110 may be formed on an inner bottom surface of the infusion drop space 121*a* of the transparent body 121, and an upper entrance of the outlet 123 may be located at a center of the fitting groove 124.

As shown in FIGS. 2 to 4, the control ball 110 may move in the vertical direction with a change in the height of a liquid level 13 formed by the infusion in the infusion drop space 121*a*, and when all of the infusion is discharged from the infusion drop space 121*a*, the bottom surface of the control ball 110 may come into close contact with the fitting groove 124 and block the upper entrance of the outlet 123. The density of the control ball 110 may be set to be lower than the density of the infusion, so that the control ball 110 can be located at the liquid level 13 formed by the infusion in the infusion drop space 121*a*. Therefore, when the infusion drop space 121*a* is sufficiently filled with the infusion, the control ball 110 may be spaced apart from the upper entrance of the outlet 123 and may not block flow of fluid discharged to the outlet 123, but when all the infusion is discharged from the infusion drop space 121*a*, the control ball 110 may fall and block the outlet 123.

The control ball 110 may include a lower member 112 whose bottom surface is in close contact with the fitting groove 124 and an upper member 111 coupled to an upper end of the lower member 112.

As an embodiment, as shown in FIG. 5A, the upper member 111 may be formed in a hemispherical shape with a flat bottom surface, and the lower member 112 may be formed in a hemispherical shape with a flat upper surface.

As another embodiment, as shown in FIG. 5B, the upper member 111 may be formed in a hemispherical shape with a flat bottom surface, and the lower member 112 may be formed in a cone shape with a flat upper surface and a vertex pointing downward.

As in the above embodiments, the shape of the lower member 112 may be formed so that a contact surface with an inner circumferential surface of the fitting groove 124 can be formed to be wide. By forming the wide contact surface between the lower member 112 and the fitting groove 124, the control ball 110 may reliably block air from being discharged from the outlet 123.

The lower member 112 may be formed of a polymer produced by linking silicon to which organic groups are bonded by a siloxane bond. Since the density of the control ball 110 must be smaller than the density of the infusion, there may be a limit to the total load of the control ball 110. In the drip infusion container 100 for the infusion device of the present disclosure, since the lower member 112 is formed of the material with excellent viscoelasticity, it may block air flowing into the outlet 123 by sufficiently contacting the fitting groove 124 even with a small load.

A lower part of the lower member 112 may be provided with a tail member (not shown) extending downward. The tail member may be provided in a cylindrical shape, and an outer diameter of the tail member may be formed to be smaller than an inner diameter of the outlet 123. For example, the outer diameter of the tail member may be formed to be less than 50% of the inner diameter of the outlet 123. A lower part of the tail member may be inserted into the outlet 123, and a length of the tail member may be longer than a length of the infusion drop space 121*a* in the vertical direction. The tail member may be provided in the lower part of the lower member 112, so that the lower member 112 can be prevented from turning upwards.

As described above, the upper member 111 may be formed of a material with higher hardness than the lower member 112, the lower member 112 may have a coupling protrusion 112*a* formed on its upper surface to be inserted into the upper member 111, and the upper member 111 may have a receiving groove 111*a* formed on its bottom surface into which the coupling protrusion 112*a* is inserted. The upper member 111 may be formed of a rigid material, and the lower member 112 may be formed of a flexible material, so that assembly for coupling between the upper member 111 and the lower member 112 may be facilitated.

A depth of the receiving groove 111*a* may be formed to be longer than a height of the coupling protrusion 112*a*, so that a hollow can be formed inside the upper member 111 when the upper member 111 and the lower member 112 are coupled. The density of the control ball 110 may be adjusted by the size of the hollow.

As shown in FIGS. 6 and 7, the coupling protrusion 112*a* may be provided in a cylindrical shape, a coupling groove 112*b* may be formed along a circumferential direction on a lower side of an outer peripheral surface of the coupling protrusion 112*a*, and an insertion protrusion 111*b* that is inserted into the coupling groove 112*b* may be formed on a lower side of an inner peripheral surface of the receiving groove 111*a*. For example, each of the coupling groove 112*b* and the insertion protrusion 111*b* may be provided in the shape of a ring, an inner diameter of the ring formed by the insertion protrusion 111*b* may be smaller than an upper outer diameter of the coupling protrusion 112*a*, and a depth of the coupling groove 112*b* may be greater than a difference between the upper outer diameter of the coupling protrusion 112*a* and the inner diameter of the ring formed by the insertion protrusion 111*b*.

As shown in FIG. 8, the method of manufacturing the control ball 110 provided in the drip infusion container 100 for the infusion device of the present disclosure may include:

- a needle insertion step of inserting a suction needle 11 from a lower side of the lower member 112 to penetrate the lower member 112 in the vertical direction;
- a coupling step of coupling the upper member 111 and the lower member 112 so that the bottom surface of the upper member 111 faces the upper surface of the lower member 112;
- a discharge step of discharging air formed in the hollow through the suction needle 11; and
- a final step of removing the suction needle 11 from the lower member 112.

A hemispherical concave portion 112*c* may be formed at an upper end of the coupling protrusion 112*a*, and in the needle insertion step, an upper end of the suction needle 11 may protrude from a center of the concave portion 112*c*. The concave portion 112*c* may be provided in a spherical shape.

In the needle insertion step, a flow path may be formed inside the suction needle 11, so that the air present in the hollow inside the control ball 110, which is formed by coupling the upper member 111 and the lower member 112, can be discharged to the outside of the control unit.

In the coupling step, the concave portion 112*c* formed in the coupling protrusion 112*a* may allow the coupling protrusion 112*a* to easily contract, thereby facilitating insertion of the coupling protrusion 112*a* into the receiving groove 111*a*.

In addition, the concave portion 112*c* may facilitate adjustment of the density of the control ball 110 by allowing the size of the hollow inside the control ball 110, which is formed by coupling the upper member 111 and the lower member 112, to be larger.

In the process of coupling the upper member 111 and the lower member 112, air in the receiving groove 111*a* may be compressed and the pressure may increase in the hollow inside the control ball 110 formed by coupling the upper member 111 and the lower member 112. The high-pressure air may separate the upper member 111 from the lower part 112. In order to prevent this, by going through the discharge step, a space of the hollow inside the control ball 110 formed by coupling the upper member 111 and the lower member 112 may be formed to have a pressure lower than atmospheric pressure.

Although embodiments according to the present disclosure have been described above, they are merely illustrative and those skilled in the art will understand that various modifications and embodiments of equivalent range are possible therefrom. Therefore, the true technical protection scope of the present disclosure should be defined by the appended claims.

EXPLANATION OF SYMBOLS

11 . . . Suction needle 13 . . . Liquid level
100 . . . Drip infusion container for infusion device 110 . . . Control ball
111 . . . Upper member 111*a* . . . Receiving groove
111*b* . . . Insertion protrusion 112 . . . Lower member
112*a* . . . Coupling protrusion 112*b* . . . Coupling groove
112*c* . . . Concave portion 120 . . . Transparent container
121 . . . Transparent body 121*a* . . . Infusion drop space
122 . . . Stopper 122*a* . . . Drip infusion hole
123 . . . Outlet 124 . . . Fitting groove
130 . . . Introduction needle

INDUSTRIAL APPLICABILITY

A drip infusion container for an infusion device of the present disclosure may be capable of preventing accidents such as air being injected to a patient when infusion is finished or there is a problem with infusion discharge from an infusion bag.

The invention claimed is:

1. A drip infusion container for an infusion device comprising:

an introduction needle which extends in a vertical direction and whose upper end is inserted into an infusion-fluid container in which infusion is stored;

a transparent container which extends in the vertical direction and receives the infusion through the introduction needle, wherein the transparent container comprises a transparent body; and a control ball which is located inside the transparent container and provided with a specific gravity lower than that of the infusion, wherein the control ball moves in the vertical direction with a change in a height of a liquid level formed by the infusion, wherein the control ball comprises a lower member and an upper member coupled to an upper end of the lower member, wherein a bottom surface of the lower member is configured to come into close contact with a fitting grove on an inner bottom surface of the transparent body, the fitting grove having the same shape as the bottom surface, wherein the lower member has a coupling protrusion formed on its upper surface to be inserted into the upper member, and the upper member has a receiving groove formed on its bottom surface into which the coupling protrusion is inserted, wherein a depth of the receiving groove is formed to be longer than a height of the coupling protrusion, so that a hollow is formed inside the upper member when the upper member and the lower member are coupled.

2. The drip infusion container of claim 1, wherein the transparent container comprises:

a stopper which is coupled to the upper end of the transparent body and to which a lower end of the introduction needle is coupled; and an outlet which is provided at a lower end of the transparent body and from which the infusion inside the transparent body is discharged, wherein the transparent body is provided with an infusion drop space extending in the vertical direction into which the infusion falls and has an open upper end.

3. The drip infusion container of claim 2, wherein the fitting groove is formed on an inner bottom surface of the infusion drop space of the transparent body, and an upper entrance of the outlet is located at a center of the fitting groove.

4. The drip infusion container of claim 3, wherein when all of the infusion is discharged from the infusion drop space, the bottom surface of the control ball comes into close contact with the fitting groove to block the upper entrance of the outlet.

5. The drip infusion container of claim 1, wherein the upper member is formed in a hemispherical shape with a flat bottom surface, and the lower member is formed in a hemispherical shape with a flat upper surface.

6. The drip infusion container of claim 1, wherein the upper member is formed in a hemispherical shape with a flat bottom surface, and the lower member is formed in a cone shape with a flat upper surface and a vertex pointing downward.

7. The drip infusion container of claim 1, wherein the lower member is made of a polymer produced by linking silicon to which organic groups are bonded by a siloxane bond.

8. The drip infusion container of claim 7, wherein the upper member is formed of a material with higher hardness than the lower member.

9. The drip infusion container of claim 1, wherein the coupling protrusion is provided in a cylindrical shape, a coupling groove is formed along a circumferential direction on a lower side of an outer peripheral surface of the coupling protrusion, and an insertion protrusion which is inserted into the coupling groove is formed on a lower side of an inner peripheral surface of the receiving groove.

10. A control ball manufacturing method for manufacturing the control ball provided in the drip infusion container for the infusion device according to claim 1, the method comprising:

a needle insertion step of inserting a suction needle from a lower side of the lower member to penetrate the lower member in the vertical direction;

a coupling step of coupling the upper member and the lower member so that the bottom surface of the upper member faces the upper surface of the lower member;

a discharge step of discharging air formed in the hollow through the suction needle; and a final step of removing the suction needle from the lower member.

11. The control ball manufacturing method of claim 10, wherein a hemispherical concave portion is formed at an upper end of the coupling protrusion, and in the needle insertion step, an upper end of the suction needle protrudes from a center of the concave portion.

* * * * *